United States Patent
Copeland et al.

(10) Patent No.: US 9,212,987 B2
(45) Date of Patent: Dec. 15, 2015

(54) ALCOHOLIC COMPOSITIONS WITH IMPROVED PROPERTIES AND METHODS FOR EVALUATING INTERACTION OF THE COMPOSITIONS WITH SURFACES

(71) Applicant: GOJO INDUSTRIES, INC., Akron, OH (US)

(72) Inventors: Amanda Jo Copeland, Seville, OH (US); Jeffrey Ross Davidson, Akron, OH (US)

(73) Assignee: GOJO INDUSTRIES, INC., Akron, OH (US)

( * ) Notice: Subject to any disclaimer, the term of this patent is extended or adjusted under 35 U.S.C. 154(b) by 231 days.

(21) Appl. No.: 13/834,532

(22) Filed: Mar. 15, 2013

(65) Prior Publication Data

US 2014/0272106 A1  Sep. 18, 2014

(51) Int. Cl.
| | |
|---|---|
| *A01N 25/16* | (2006.01) |
| *G01N 19/00* | (2006.01) |
| *B05D 5/00* | (2006.01) |
| *B05D 7/00* | (2006.01) |
| *A01N 31/02* | (2006.01) |
| *G01N 19/04* | (2006.01) |
| *G01N 21/00* | (2006.01) |

(52) U.S. Cl.
CPC ............... *G01N 19/00* (2013.01); *A01N 31/02* (2013.01); *B05D 5/00* (2013.01); *B05D 7/52* (2013.01); *B05D 7/544* (2013.01); *G01N 19/04* (2013.01); *G01N 21/00* (2013.01); *B05D 2320/10* (2013.01)

(58) Field of Classification Search
None
See application file for complete search history.

(56) References Cited

U.S. PATENT DOCUMENTS

| | | |
|---|---|---|
| 2,327,495 A | 8/1943 | Budner |
| 4,230,605 A | 10/1980 | Connolly et al. |
| 4,537,802 A | 8/1985 | Flanagan |
| 5,409,639 A | 4/1995 | Fusiak et al. |
| 5,750,579 A | 5/1998 | Kamishita et al. |
| 6,228,385 B1 | 5/2001 | Shick |
| 7,235,230 B2 | 6/2007 | LeGrow et al. |
| 2003/0086888 A1 | 5/2003 | LeGrow et al. |
| 2004/0241196 A1 | 12/2004 | Popoff |
| 2008/0264445 A1 | 10/2008 | Levitt et al. |
| 2008/0292574 A1 | 11/2008 | Uehara |
| 2010/0012132 A1 | 1/2010 | Harrison et al. |

*Primary Examiner* — William Phillip Fletcher, III
(74) *Attorney, Agent, or Firm* — Renner Kenner Greive Bobak Taylor & Weber Co. LPA

(57) ABSTRACT

A method is provided for measuring the interaction of a disinfecting composition with a floor wax. The method include coating a surface with floor wax, allowing the coating to dry, applying a selected amount of disinfecting composition to the coated surface, and measuring, after a pre-determined amount of time, the tack of the surface, by using a controlled force measurement inverted probe machine. A detectable amount of tack indicates that the disinfecting composition has interacted with the floor wax. Alternatively, any tacky residue on the dried product surface may be sampled and analyzed by Fourier transform spectroscopy. Absorption at a wavelength associated with the floor wax indicates that the product has interacted with the floor wax. A foamable disinfecting composition having reduced interaction with floor wax is also provided.

14 Claims, No Drawings

ALCOHOLIC COMPOSITIONS WITH IMPROVED PROPERTIES AND METHODS FOR EVALUATING INTERACTION OF THE COMPOSITIONS WITH SURFACES

TECHNICAL FIELD

Embodiments of the present invention provide methods for evaluating the interaction of disinfecting compositions with surfaces upon which the compositions may be dripped or splashed. Embodiments of the present invention provide alcoholic disinfecting compositions with reduced interaction with floor wax.

BACKGROUND OF THE INVENTION

Alcoholic disinfectants have been shown to be efficacious broad-spectrum antimicrobial products, and are widely used in healthcare settings and many other public, high traffic areas. Foam cleaning products are popular, in part because they are easier to spread on surfaces. Disinfectants are often dispensed from wall-mounted dispensers, and are used in many locations that have waxed flooring.

If the product drips or splashes onto the floor, sticky spots may result, that attract dust and grime. Some alcohol-based disinfection products may contain tacky polymers or other tacky ingredients that remain on the floor where the product has dripped, after the alcohol has evaporated. Some alcohol-based disinfection products may contain ingredients that interact with the floor wax to create sticky spots.

Unfortunately, the sticky spots can attract dirt, which can be unsanitary and unsightly, and also can be difficult to remove with normal floor cleaning apparatus and products.

Thus, there is a need in the art for an foamable alcoholic product that has reduced interaction with floor wax.

SUMMARY OF THE INVENTION

Embodiments of the present invention provide a method for measuring the interaction of an alcoholic disinfecting composition with a floor wax, the method comprising the steps of coating a surface with floor wax, allowing the coating to dry, applying an amount of the disinfecting composition to the coated surface, sufficient to form a thin layer over the coated surface, allowing the disinfecting composition to dry, thereby forming a disinfectant layer, sampling the disinfectant layer, by swabbing or blotting the disinfectant layer, testing the sample by Fourier Transform Infrared analysis, measuring the absorption of the sample at a pre-selected wavelength that correlates to the floor wax control and that does not correlate to the disinfecting composition, wherein measurable absorbance at said wavelength indicates that interaction has occurred.

Embodiments of the present invention further provide a foamable disinfecting composition comprising at least about 40 wt. % of a C1-6 alcohol, based upon the total weight of the disinfecting composition; a foaming surfactant selected from the group consisting of fluorosurfactants and siloxane-based polymer surfactants; and from about 0.4 to about 5 wt. % of glycerin, based upon the total weight of the composition, wherein the composition exhibits reduced interaction with floor wax when compared to the same composition but containing less than about 0.4 wt. % of glycerin, based upon the total weight of the composition.

Embodiments of the present invention further provide a method for measuring the interaction of a disinfecting composition with a floor wax, the method comprising the steps of coating a surface with floor wax, allowing the coating to dry, applying a selected amount of disinfecting composition to the coated surface, and measuring, after a pre-determined amount of time, the tack of the surface, by using a controlled force measurement inverted probe machine, wherein a detectable amount of tack indicates that the disinfecting composition has interacted with the floor wax.

DETAILED DESCRIPTION OF ILLUSTRATIVE EMBODIMENTS

In one or more embodiments, the present method provides a foamable alcoholic disinfecting composition. The disinfecting composition includes alcohol, a foaming surfactant, and glycerin.

In one or more embodiments, the alcohol is a lower alcohol, i.e. an alcohol containing 1 to 6 carbon atoms. Typically, these alcohols have antimicrobial properties. Examples of lower alcohols include, but are not limited to, methanol, ethanol, propanol, butanol, pentanol, hexanol, and isomers and mixtures thereof. In one or more embodiments, the alcohol comprises ethanol, propanol, or butanol, or isomers or mixtures thereof. In particular embodiments, the alcohol comprises ethanol.

In one or more embodiments, the composition comprises at least 40 percent by weight (wt. %) $C_{1-6}$ alcohol, based upon the total weight of the composition, in other embodiments, at least 50 wt. %, in other embodiments, at least 60 wt. %, in other embodiments, at least 70 wt. %, in yet other embodiments, at least 80 wt. %, and in other embodiments, at least 90 wt. % alcohol, based upon the total weight of composition. More or less alcohol may be required in certain instances, depending particularly on other ingredients and/or the amounts thereof employed in the composition. In one or more embodiments, the composition comprises from about 50 to about 99 wt. % of $C_{1-6}$ alcohol, in other embodiments, from about 60 to about 98 wt. %, in yet other embodiments, from about 70 to about 97 wt. %, and in still other embodiments, from about 80 to about 96 wt. % of $C_{1-6}$ alcohol, based upon the total weight of the composition.

The foaming surfactant contributes foaming properties to the disinfecting composition, and may include anionic, cationic, nonionic, zwitterionic, or amphoteric surfactants and their associated salts. In one embodiment, the foaming surfactant includes a fluorosurfactant, a siloxane-based surfactant, or a combination thereof. Fluorosurfactants include compounds that contain at least one fluorine atom. Examples of fluorosurfactants include perfluoroalkylethyl phosphates, perfluoroalkylethyl betaines, fluoroaliphatic amine oxides, fluoroaliphatic sodium sulfosuccinates, fluoroaliphatic stearate esters, fluoroaliphatic phosphate esters, fluoroaliphatic quaternaries, fluoroaliphatic polyoxyethylenes, and the like, and mixtures thereof.

Siloxane-based foaming surfactants are further described in U.S. Pat. Nos. 8,383,686, 8,309,111, 8,304,375, 8,263,098, 8,124,115, 8,058,315, 7,842,725, and 7,651,990, as well as U.S. Pat. Published App. No. 2007/0148101, all of which are incorporated by reference.

In one or more embodiments, the siloxane-based foaming surfactant is a siloxane polymer surfactant. Siloxane polymer surfactants may be generally characterized by containing one or more Si—O—Si linkages in the polymer backbone. The siloxane polymer surfactant may or may not include a fluorine atom. Therefore, some foaming surfactants may be classified as both fluorosurfactants and siloxane polymer surfactants. Siloxane polymer surfactants include organopolysiloxane dimethicone polyols, silicone carbinol fluids, silicone poly-ethers, alkylmethyl siloxanes, amodimethicones, trisiloxane ethoxylates, dimethiconols, quaternized silicone surfactants, polysilicones, silicone crosspolymers, and silicone waxes.

Examples of siloxane polymer surfactants include dimethicone PEG-7 undecylenate, PEG-10 dimethicone, PEG-8 dimethicone, PEG-12 dimethicone, perfluorononylethyl carboxydecal PEG 10, PEG-20/PPG-23 dimethicone, PEG-11 methyl ether dimethicone, bis-PEG/PPG-20/20 dimethicone, silicone quats, PEG-9 dimethicone, PPG-12 dimethicone, fluoro PEG-8 dimethicone, PEG 23/PPG 6 dimethicone, PEG 20/PPG 23 dimethicone, PEG 17 dimethicone, PEG5/PPG3 methicone, bis PEG20 dimethicone, PEG/PPG20/15 dimethicone copolyol and sulfosuccinate blends, PEG-8 dimethicone\dimmer acid blends, PEG-8 dimethicone\fatty acid blends, PEG-8 dimethicone\cold pressed vegetable oil\polyquarternium blends, random block polymers and mixtures thereof.

In one embodiment, the siloxane polymer surfactant includes a compound that may be represented by the formula

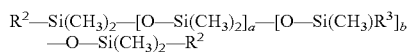

where $R^2$ and $R^3$ independently include a methyl group or a moiety that may be represented by the formula

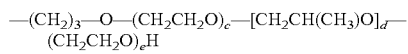

with the proviso that both $R^2$ and $R^3$ are not $CH_3$, where a is an integer from about 3 to about 21, b is an integer from about 1 to about 7, c is an integer from about 0 to about 40, d is an integer from about 0 to about 40, and e is an integer from about 0 to about 40, with the proviso that $a \geq 3 \times b$ and that $c+d+e \geq 5$.

The amount of foaming surfactant is not particularly limited, so long as an effective amount to produce foaming is present. In certain embodiments, the effective amount to produce foaming may vary, depending upon the amount of alcohol and other ingredients that are present. In one or more embodiments, the alcoholic composition includes at least about 0.002 wt. % of foaming surfactant, based upon the total weight of the alcoholic composition. In another embodiment, the disinfecting composition includes at least about 0.01 wt. % of foaming surfactant, based upon the total weight of the disinfecting composition. In yet another embodiment, the disinfecting composition includes at least about 0.05 wt. % of foaming surfactant, based upon the total weight of the disinfecting composition.

In one embodiment, the foaming surfactant is present in an amount of from about 0.002 to about 4 weight percent, based upon the total weight of the disinfecting composition. In another embodiment, the foaming surfactant is present in an amount of from about 0.01 to about 2 weight percent, based upon the total weight of the disinfecting composition. It is envisioned that higher amounts may also be effective to produce foam. All such weights as they pertain to listed ingredients are based on the active level and, therefore, do not include carriers or by-products that may be included in commercially available materials, unless otherwise specified.

In one or more embodiments, the foaming surfactant is added directly to the disinfecting composition. In other embodiments, the foaming surfactant is added to the disinfecting composition as a solution or emulsion. In other words, the foaming surfactant may be premixed with a carrier to form a foaming surfactant solution or emulsion, with the proviso that the carrier does not deleteriously affect the foaming properties of the disinfecting composition. Examples of carriers include water, alcohol, glycols such as propylene or ethylene glycol, ketones, linear and/or cyclic hydrocarbons, triglycerides, carbonates, silicones, alkenes, esters such as acetates, benzoates, fatty esters, glyceryl esters, ethers, amides, polyethylene glycols and PEG/PPG copolymers, inorganic salt solutions such as saline, and mixtures thereof. It will be understood that, when the foaming surfactant is premixed to form a foaming surfactant solution or emulsion, the amount of solution or emulsion that is added to the disinfecting composition may be selected so that the amount of foaming surfactant falls within the ranges set forth hereinabove.

Advantageously, it has been discovered that glycerin, when present in sufficient amount, decreases the amount of interaction of the composition with floor wax.

In one or more embodiments, the amount of glycerin is at least about 0.4 wt. %, based upon the total weight of the disinfecting composition, in other embodiments, at least about 0.5 wt. %, and in other embodiments, at least about 0.6 wt. %, based upon the total weight of the disinfecting composition.

In one or more embodiments, the amount of glycerin is from about 0.4 to about 5 wt. %, in other embodiments, from about 0.5 to about 3, and in other embodiments, from about 0.6 to about 2 wt. %, based upon the total weight of the disinfecting composition.

It is believed that the siloxane polymer surfactant may contribute to the tackiness of the composition, and/or to the interaction with the floor wax to produce a tacky residue. Thus, in one or more embodiments, the amount of glycerin may advantageously be selected relative to the amount of siloxane polymer surfactant. In these or other embodiments, the amount of glycerin relative to the amount of siloxane polymer surfactant, on a weight basis, is from about 1:0.5 to about 1:7.

In one or more embodiments, the balance of the composition is water. In other embodiments, the composition may include one or more optional ingredients, with the proviso that there is no deleterious effect on the foaming or antimicrobial efficacy of the antimicrobial foam.

As described hereinabove, the disinfecting composition of this invention includes a number of ingredients that combine to produce an antimicrobial alcoholic foam having reduced interaction with floor wax. The disinfecting composition may further comprise a wide range of optional ingredients, with the proviso that they do not deleteriously affect the foaming or sanitizing efficacy of the compositions, and does not increase the proclivity of the composition to interact with floor wax. The CTFA International Cosmetic Ingredient Dictionary and Handbook, Eleventh Edition 2005, and the 2004 CTFA International Buyer's Guide, both of which are incorporated by reference herein in their entirety, describe a wide variety of non-limiting cosmetic and pharmaceutical ingredients commonly used in the skin care industry, that are suitable for use in the compositions of the present invention. Non-limiting examples of functional classes of ingredients are described at page 537 of this reference. Examples of these functional classes include: abrasives, anti-acne agents, anti-caking agents, antioxidants, binders, biological additives, bulking agents, chelating agents, chemical additives; colorants, conditioners, cosmetic astringents, cosmetic biocides, denaturants, drug astringents, emulsifiers, external analgesics, film formers, fragrance components, humectants, moisturizers, opacifying agents, plasticizers, preservatives (sometimes referred to as antimicrobials), propellants, reducing agents, skin bleaching agents, skin-conditioning agents (emollient, miscellaneous, and occlusive), skin protectants, solvents, surfactants, foamableboosters, hydrotropes, solubilizing agents, suspending agents (nonsurfactant), sunscreen agents, ultraviolet light absorbers, detackifiers, and viscosity increasing agents (aqueous and nonaqueous). Examples of other functional classes of materials useful herein that are well known to one of ordinary skill in the art include sequestrants, keratolytics, topical active ingredients, and the like.

In certain embodiments, the disinfecting composition of the present invention further includes at least one foam enhancer. In one or more embodiments, the disinfecting compositions of these embodiments exhibit improved foam stability when compared to an disinfecting composition without the foam enhancer. By "foam stability" is meant the length of time that it takes for a foam to break down into a liquid.

In these or other embodiments, the disinfecting compositions of these embodiments exhibit improved foam quality when compared to an disinfecting composition without the foam enhancer. By "foam quality" is meant the quantity and size of the foam bubbles. Foams with improved foam quality may be characterized by a greater number of smaller bubbles, which contributes to a creamy, dense appearance.

Polymeric foam enhancers include polyquaternium polymers. In general, a polyquaternium polymer is one that is designated as such by the CTFA. Polyquaternium polymers may be characterized by containing a quaternary ammonium group. In one or more embodiments, the foam enhancer includes a poly(ethylene oxide) polymer, a poloxamer, hydroxyethyl cellulose, hydroxypropyl cellulose, or a combination thereof.

In one or more embodiments, the foam enhancer includes a poly(ethylene oxide) polymer having an average molecular weight in the range from about 100,000 to about 10,000,000, in other embodiments from about 200,000 to about 4,000,000. In one or more embodiments, the primary foam enhancer includes a poly(ethylene oxide) polymer selected from PEG-4 to PEG-100. Examples of commercially available poly(ethylene oxide) polymers suitable for use as a foam enhancer include POLYOX™ products, available from Dow Chemical, such as WSR N-80, WSR N12K, WSR N60K, and WSR-301.

Still other foam enhancers are described in U.S. Pat. Nos. 8,383,686, 8,309,111, 8,304,375, 8,263,098, 8,124,115, 8,058,315, 7,842,725, and 7,651,990, as well as U.S. Pat. Published App. No. 2007/0148101, which are incorporated by reference herein.

In one or more embodiments, the composition includes up to about 10 wt. % of the primary foam enhancer. In one or more embodiments, the composition includes from 0 to about 10 wt. %, in other embodiments, from about 0.001 to about 8 wt. %, in other embodiments, from about 0.01 to about 5 wt. %, in other embodiments, from about 0.01 to about 1 wt. %, based upon the total weight of the disinfecting composition.

In one embodiment, foam stabilizer is present in an amount of from about 0.005 to about 4 weight percent active, based upon the total weight of the disinfecting composition. In another embodiment, the foam stabilizer is present in an amount of from about 0.01 to about 1 weight percent, based upon the total weight of the disinfecting composition, and in yet another embodiment, the foam stabilizer is present in an amount of from about 0.02 to about 0.2 weight percent, based upon the total weight of the disinfecting composition.

In certain embodiments, the disinfecting composition comprises one or more humectants. Examples of humectants include propylene glycol, dipropyleneglycol, hexylene glycol, 1,4-dihydroxyhexane, 1,2,6-hexanetriol, sorbitol, butylene glycol, propanediols, such as methyl propane diol, dipropylene glycol, triethylene glycol, polyethylene glycols, ethoxydiglycol, polyethylene sorbitol, and combinations thereof. Other humectants include glycolic acid, glycolate salts, lactate salts, lactic acid, sodium pyrrolidone carboxylic acid, hyaluronic acid, chitin, and the like.

In one or more embodiments, the foamable alcoholic composition has a viscosity of less than about 500 centipoise (cps), in other embodiments, less than about 200 cps, in other embodiments, less than about 100 cps, as measured by Brookfield RV Viscometer using RV and/or LV Spindles at 22° C.+/−3° C.

In one or more embodiments, the disinfecting composition includes one or more antiviral agents or antiviral enhancers. Examples of antiviral enhancers include cationic oligomers and polymers, chaotropic agents, and copper and zinc compounds. Antiviral enhancers are further described in U.S. Pat. No. 8,119,115 and co-pending U.S. Patent Application Publications 2007/0185216, and 2009/0018213, all of which are hereby incorporated by reference.

In one or more embodiments, the foamable alcoholic composition may contain one or more auxiliary antimicrobial agents, where the term "auxiliary" refers to agents other than the $C_{1-6}$ alcohol, and the term "antimicrobial agents" includes preservatives.

Examples of auxiliary antimicrobial agents include, but are not limited to, triclosan, also known as 5 chloro 2(2,4 dichlorophenoxy) phenol and available from Ciba Geigy Corporation under the tradename IRGASAN®; chloroxylenol, also known as 4 chloro 3,5 xylenol, available from Nipa Laboratories, Inc. under the tradenames NIPACIDE® MX or PX; hexetidine, also known as 5 amino 1,3 bis(2 ethylhexyl) 5 methyl hexahydropyrimidine; chlorhexidine salts including chlorhexidine gluconate and the salts of N,N" Bis(4 chlorophenyl) 3,12 diimino 2,4,11,14 tetraazatetradecanediimidiamide; 2-bromo-2 nitropropane-1,3-diol, 1,2-hexanediol, 1,2-octanediol, 1,2-decanediol, benzalkonium chloride; cetylpyridinium chloride; alkylbenzyldimethylammonium chlorides; iodine; phenol derivatives, povidone iodine including polyvinylpyrrolidinone iodine; parabens; hydantoins and derivatives thereof, including 2,4 imidazolidinedione and derivatives of 2,4 imidazolidinedione as well as dimethylol 5,5 dimethylhydantoin (also known as DMDM hydantoin or glydant); phenoxyethanol; cis isomer of 1 (3 chloroallyl) 3,5,6 triaza 1 azoniaadamantane chloride, also known as quaternium 15 and available from Dow Chemical Company under the tradename DOWCIL™ 2000; diazolidinyl urea; benzethonium chloride; methylbenzethonium chloride; transition metal compounds such as silver, copper, magnesium, zinc compounds; hydrogen peroxide, chorine dioxide, and mixtures thereof. In one or more embodiments, the amount of each individual auxiliary antimicrobial agent may be from 0 to about 2 wt. %, in other embodiments, from about 0.1 to about 1 wt. %, based upon the total weight of the disinfecting composition.

In one or more embodiments, the disinfecting composition may be prepared by simply mixing the ingredients together. As would be known in the art, it is advantageous to add any water-soluble ingredients to the water prior to adding the alcohol, after which any alcohol-soluble ingredients may be added. Of course, it is also possible to pre-mix the alcohol-soluble ingredients with the alcohol, and then add the pre-mix to the water mixture.

The present invention provides foamable alcoholic compositions that are foamable without the need for propellants or pressurized dispensers. That is, the foams of the present invention are non-aerosol foams. Embodiments of the present invention provide foamable alcoholic compositions that produce a foam when mixed with ambient air or an inert gas and passed through a mesh screen.

Hard surface flooring for high traffic areas is selected for durability and ease of maintenance. Types of flooring includes wood, stone, synthetic wood, high-performance rubber, terrazzo, vinyl, and vinyl composite tile.

Vinyl composition tile (VCT) is a finished flooring material used primarily in commercial and institutional applications. Tiles are typically waxed, i.e. coated with a floor finish composition, and the coating is allowed to dry. Optionally, the dry floor coating may be buffed, i.e. burnished.

Commercially available floor finish compositions typically are aqueous emulsion-based polymer compositions comprising one or more organic solvents, plasticizers, coating aides, anti-foaming agents, polymer emulsions, metal complexing agents, waxes, and the like. The polymer composition is applied to a floor surface and then allowed to dry in air, normally at ambient temperature and humidity. A coating, i.e. film, is formed that serves as a protective barrier against soil deposited on the floor by pedestrian traffic, for example. For purposes of this disclosure, floor finish compositions will generally be referred to as floor waxes.

As described above, floor waxes are not completely impervious to alcoholic compositions that may be dripped or spilled onto the floor. Surprisingly, the alcoholic disinfectant compositions of the present invention have reduced interaction with the floor wax.

In one or more embodiments, the interaction of an alcoholic disinfecting composition with a floor wax may be evaluated by providing a dry surface coated with floor wax, applying a selected amount of disinfecting composition to the coated surface, and then measuring, after a pre-determined amount of time, the tackiness of the surface. Tack, which generally indicates the stickiness or adhesiveness of a substance, can be measured, for example, by using a controlled force measurement inverted probe machine, such as the Probe Material Analyzer PMA-1000, available from ChemInstruments International. In one or more embodiments, the probe is stainless steel. In one or more embodiments, the measurements are taken under conditions of standard temperature and pressure.

Advantageously, the present invention provides a method for measuring the amount of tackiness created by interaction of a disinfecting composition with a floor wax. The method includes the steps of coating a surface with floor wax, allowing the coating to dry, applying a selected amount of disinfecting composition to the coated surface, and measuring, after a pre-determined amount of time, the tackiness of the surface, by using a controlled force measurement inverted probe machine. The amount of time that the disinfecting composition is in contact with the floor wax before the tackiness is measured may be referred to as the contact time. As a control, a measurement may be made of the coated surface that has not come into contact with any disinfecting composition. A comparative measurement could be made between two or more compositions, and the reduction in tackiness could be quantified for the composition that resulted in relatively less tackiness. In one or more embodiments, the amount of disinfecting composition is selected to provide a thin coating that covers the surface of the floor wax. In one or more embodiments, the pre-determined amount of time for which the disinfecting composition remains in contact with the floor wax before being tested is about 24 hours, in other embodiments, 1 week, and in other embodiments, 2 weeks.

In one or more embodiments, the disinfecting compositions of the present invention do not interact with floor wax over a contact time of two weeks to produce a tack of more than 130 grams, when measured at standard temperature and pressure, using a controlled force measurement inverted probe machine having a stainless steel flat probe having a diameter of about 0.187 inches, and applying about 100 grams of force for about 5 seconds. In other embodiments, the tack is less than about 100 grams, when measured under these conditions, in other embodiments, less than about 70 grams, in other embodiments, less than about 50 grams, and in other embodiments, less than about 40 grams.

The present invention further provides a method for evaluating the interaction of a disinfecting composition with a floor itself, as well as for any other surface. In one or more embodiments, the interaction of an alcoholic disinfecting composition with a floor or other surface may be evaluated by providing a portion of the surface, applying a selected amount of disinfecting composition to the surface, and then measuring, after a pre-determined amount of time, the tackiness of the surface, for example, by using a controlled force measurement inverted probe machine, such as the Probe Material Analyzer PMA-1000, as described above.

In one or more embodiments, the interaction of an alcoholic disinfecting composition with a floor wax may be evaluated by coating a surface with floor wax, allowing the coating to dry, applying an amount of the disinfecting composition to the coated surface, sufficient to form a thin layer over the coated surface, allowing the disinfecting composition to dry, thereby forming a disinfectant layer, sampling the disinfectant layer, and testing the sample by Fourier Transform Infrared analysis (FTIR). In one or more embodiments, the sampling may be done by swabbing or blotting the disinfectant layer. In one or more embodiments, two control samples may be tested by FTIR, with one control being the floor wax and the other control being the disinfecting composition. At least one wavelength may be identified at which the floor wax exhibits an absorption but the disinfecting composition does not. By comparing the test samples with the controls, samples that have interacted with the floor wax may exhibit an absorption at a wavelength that correlates to the floor wax control and that does not appear in the disinfecting composition. Measurement of the absorbance at the wavelength may indicate whether or not interaction has occurred, such that some amount of the floor wax has become mixed with the disinfectant layer. Quantification of the absorbance at this wavelength may indicate the amount of interaction that has occurred.

Places on a waxed floor surface where disinfecting composition has dripped or splashed and then interacted with the floor wax to produce a tacky spot can be more likely to accumulate dirt and grime than surrounding areas, thereby resulting in dark spots on the floor. These spots may be distinguished from spots that result from regular soiling in that, because of the interaction that has occurred with the floor wax, these spots are more difficult to remove with routine cleaners and routine floor cleaning regimens and equipment. Thus, in one or more embodiments, the interaction of an alcoholic disinfecting composition with a floor wax may be evaluated by a method wherein spots of test product are placed on a waxed floor as described in the following method.

Embodiments of the present invention further provide a floor spotting test method. In one or more embodiments, the method includes the steps of: (A) selecting and preparing a floor surface, (B) applying a test product on the floor surface, (C) exposing the floor surface to pedestrian traffic, wherein said traffic creates one or more spots on the floor surface, (D) evaluating the spots, and (E) cleaning the floor surface to remove the spots.

(A) Floor Selecting and Preparation

In one or more embodiments, the selected floor surface is a vinyl composite tile (VCT) floor surface. VCT floors are commonly used in most hospital hallways and in other commercial buildings. The most common size of each tile is twelve inches by twelve inches, however VCT flooring is also available in 6 foot to 12 foot widths, and rolls of various foot lengths are available and may also be tested according to the method of the invention.

A section of floor material is obtained for testing. In one or more embodiments, a six square foot section is employed. The section may unrolled and cut, if necessary, to achieve the desired size. If the section is obtained from a roll, the section may be turned upside down and allowed to relax over a 24-hour period. Once the floor section has relaxed into a relatively flat position, the section may be turned over and cleaned.

In one or more embodiments, where a new, unused sample of floor material is selected for testing, there may be a factory coating on the floor material that must be removed. The selected section of floor material should be swept to remove dirt, dust, etc. The factory coating may be removed as following. The section should be wetted with a cleaning solution. In one or more embodiments, the section is wetted with Neutral Cleaner 310E, available from Ecolab, diluted in clean water in an amount of about 0.010 ounces (oz.) per gallon of water.

In one or more embodiments, the section of floor is then scrubbed with a floor scrubber such as Tennant F Series scrubber Model F-10, using a 3M 3100 Aqua Burnish Green pad. Once the factory coating is removed, excess water should be removed, for example with a wet vac squeegee (Tennant Scrubber-Dryer T5 Fast), or mopped off with a clean mop. The section should then be mopped with clean water, and allowed to air dry. A fan may be employed, if desired.

If a used floor section is selected for testing, any wax coating should be stripped from the surface, and the section should be cleaned as described above.

In one or more embodiments, a floor wax is applied to the dry, clean test section. In one or more embodiments, a rayon or sponge mop may be employed. In one or more embodiments, the mop is dipped into the wax floor finish, and then slowly spread over the test section. Care should be taken to cover the entire surface of the test section, and to apply an even coating.

The wax coated test section is allowed to air or fan dry, according to the floor wax manufacturer's instructions, or until the coated test section does not feel sticky to the touch. In one or more embodiments, the coating is allowed to dry for from about 30 to about 60 minutes. In one or more embodiments, additional coats of wax may be applied. The number of coats is not limited, but generally may be selected to achieve the percent solids that is recommended by the floor wax manufacturer. In one or more embodiments, 4 coats of wax are applied to the test section. The test section is allowed to dry for a final time period as recommended by the floor wax manufacturer. In one or more embodiments, the test section is allowed to dry for from about 24 to about 48 hours.

In one or more embodiments, once the wax coated test section has dried, the section is mopped with a dust mop to remove any loose dirt. If necessary, the test section may be wet-mopped to remove additional dirt. Once the wax coated test section is clean, it may be burnished, i.e. buffed, for example by using a Nobles Speedshine 1600 burnisher with a 3M 3600 Eraser Burnish (Pink) Pad. In one or more embodiments, one or two passes may be made over the surface of the floor section. Care should be taken to ensure that the floor is generally flat and level, so that the wax is not unevenly removed. In one or more embodiments, burnishing the test section provides results that are similar to polishing a floor, that is, burnishing hardens the cured wax coating and enhances the shine.

(B) Formulation Application:

In one or more embodiments, a grid is established on the test section, and the test product is applied to the test section relative to the grid. The method of the invention is not limited to any particular grid or arrangement of test product on the test section. The following description is provided for illustrative purposes only. In one or more embodiments, the configuration of the grid may be selected based upon the number of products to be tested. In one or more embodiments, a 6 foot by 6 foot test section is able to accommodate up to 18 samples, spaced at 5 inch intervals. A random number generator may be used to determine the location of each product to be tested.

In one or more embodiments, the test sheet may be immobilized to enable accurate measurement and application of the test products, by adhering the test sheet to a flat surface. Product is applied to the test sheet, carefully measuring as necessary to ensure that the product is located on the test sheet according to the grid.

A measured amount of product is applied. The amount of product is not necessarily limited, but each product should be applied in the same amount. In one or more embodiments, about 0.5 milliliters (ml) of product is applied to the test sheet.

The product is allowed to dry. In one or more embodiments, the product is allowed to dry for from about 12 to about 18 hours. Initial observations of the product may be recorded, including such features as the dispersion of the formulation (spot shape) and the amount of the formulation that appears dry. Additional characterizations may include the tack of the spot, determined by gently touching an edge of the formulation/wax interface.

(C) Traffic Exposure

In one or more embodiments, the test sheet is positioned in an area that receives a large amount of pedestrian traffic, and adhered to the floor. Notations may be made of the row, column orientation in relation to the positioning. Other information that may be recorded includes the type(s) of surfaces surrounding the building in which the test sheet is placed, the temperature, date and other weather conditions (Rain, Snow, Dusty, etc.). All of these factors may potentially affect the amount and type of dirt and debris that may be tracked across the test sheet.

In one or more embodiments, a traffic count of about 1000 is sufficient for the testing purposes. If pedestrian traffic is not expected to be uniform over all portions of the test sheet, the test sheet may be rotated at specified intervals. In one or more embodiments, the traffic count is about 1000 during an 8 to 10 hour test period, and the test sheet is rotated about 90 degrees once every 2 to 2.5 hours.

In one or more embodiments, an observer may monitor traffic and use a counter to record traffic patterns. In one or more embodiments, photographs may be taken at various intervals to document the maturation of the product spots.

In one or more embodiments, the test sheet is exposed to pedestrian traffic for a pre-determined amount of time. In other embodiments, the exposure time may continue until the majority of the spots are mature. In one or more embodiments, a mature spot is one in which one of the following conditions have been met: (1) the test spot is dark enough to be visually distinguished from the other test spots; or (2) the test spot is no longer continuing to accumulate dirt or grime.

When the pre-determined test period is over and/or the majority of the sports are mature, the test section may be relocated to a location where it can be closely viewed and the spots may be evaluated.

(D) Spot Evaluation

In one or more embodiments, each spot may be evaluated for dryness and spot shape. In one or more embodiments, the characteristics of the spot after exposure to pedestrian traffic may be compared to the initial characteristics of the spot.

In one or more embodiments, the color of the spot may be rated against a color scale. For examples, using the Pantone® Color Cue® 2, the spot may be measured using the Hunter-Lab L a*b* colorscale. A Hunter L reading of 0 indicates that the sample is Black; a reading of 100 indicates that the sample is White.

In one or more embodiments, photographs may be taken of each spot. For example, using a ring light source, camera and tripod, high contrast pictures of each spot may be recorded for further comparisons.

In one or more embodiments, a panel of judges may grade each spot by using a customized HunterLab L scale, wherein reference photographs depict each HunterLab L reading. In one or more embodiments, a scale of 0 to 5 is employed. Ratings from each judge may be compiled and averaged for each product tested.

(E) Spot Cleanability

Advantageously, the present invention provides a method whereby it is not only possible to evaluate products for their proclivity to interact with floor wax in a manner that forms a residue on the floor that attracts dirt, but the method also makes it possible to evaluate products for their proclivity to interact with floor wax in a manner that forms a residue on the floor that cannot be easily removed.

Thus, in one or more embodiments, the method includes the further step of comparing the clean-ability of the test product, or in other words, evaluating the ease or difficulty of removing the product from the test section after it has been in contact with the test section and exposed to pedestrian traffic.

In one or more embodiments, a spot is subjected to one or more of the following cleaning protocols, and then evaluated as described above. (1) Scraping—gently scrape the spot using a scraper or a mild abrasive pad, such as 3M Scotch-Bright™ Non-Scratch Scrub Sponge; (2) Mr. Clean® Magic eraser—rub over spots in a consistent manner; (3) Cleaning solutions by hand—use any of the commercially available cleaners; (4) Auto scrubbing—Use a machine such as the Tennant® T5 Auto scrubber with a red buffing/cleaning pad, along with any of the commercially available cleaners.

The present invention further provides a further method for evaluating the interaction of a disinfecting composition with a floor itself, as well as for any other surface. In one or more embodiments, the interaction of an alcoholic disinfecting composition with a floor or other surface may be evaluated by providing a portion of the surface, applying an amount of the disinfecting composition to the coated surface, sufficient to form a thin layer over the coated surface, allowing the disinfecting composition to dry, thereby forming a disinfectant layer, sampling the disinfectant layer, and testing the sample by FTIR, as described above.

Advantageously, embodiments of the present invention provide foamable disinfecting compositions that have reduced interaction with floor wax, when compared to the same composition but containing lower amounts or no amount of glycerin. Surprisingly, higher levels of glycerin, a substance that has been used in the past to increase tack, leads to disinfecting compositions that do not become tacky when dripped or splashed onto a waxed floor.

Additionally, embodiments of the present invention have improved properties such as reduced interaction with floor wax, while not sacrificing foam quality or stability.

Methods of the present invention can advantageously be employed to evaluate products for their proclivity to interact with floor wax. It will be understood that variations of the methods disclosed herein may be employed to evaluate a wide variety of products, and their interaction with a wide variety of surfaces and surface coatings.

In order to demonstrate the practice of the present invention, the following examples have been prepared and tested. The examples should not, however, be viewed as limiting the scope of the invention. The claims will serve to define the invention.

Examples

Examples 1-10 were prepared by combining ingredients in the amounts shown in the following tables. Samples were tested for interaction with floor wax as indicated by either FTIR analysis or tack testing, according to methods described below. The floor wax utilized in this testing was JohnsonDiversey High Mileage Floor Finish, although similar trends were observed in testing with Betco Corporation Untouchable and Hard As Nails floor finishes.

Samples were prepared for FTIR and tack testing as follows. About 5 grams of floor wax was placed in an aluminum pan and allowed to dry for at least 24 hours. About 15 drops of test product was placed onto the dried floor wax, and allowed to dry. The contact time, i.e. the amount of time that the test product was in contact with the floor wax prior to testing, was either overnight, 24 hours, or 2 weeks, as indicated in the tables below.

After the desired contact time had been reached, samples were then prepared for FTIR testing as follows. A piece of aluminum foil was touched to the dried sample, with light pressure, such that any tacky material that had formed from interaction between the sample and the floor wax was transferred to the piece of aluminum foil.

The tacky material was analyzed by FTIR, and the absorption at ~1724 $cm^{-1}$ (a wavelength that correlates to the floor wax) was quantified. Results are reported below.

Also after the desired contact time, samples were tested for tack as follows. Using a Chemsultants International Probe Material Analyzer PMA-1000, equipped with a 3/16" diameter flat probe tip, about 100 grams of force was applied onto each sample for 5 seconds dwell time, and the retraction force was measured. In most cases, multiple readings were taken and averaged. Results are shown below.

TABLE 1

| INGREDIENTS (wt. %) | EXAMPLE 1 | EXAMPLE 2 |
|---|---|---|
| SDA 3C ethanol | 74.1 | 74.1 |
| PEG-12 dimethicone | 1.75 | 1.75 |
| Glycerin | 1.5 | 1.0 |
| Caprylyl glycol | 0.5 | 0.5 |
| Fragrance | 0.075 | 0.075 |
| Water | q.s. | q.s. |
| FTIR (1 day contact time) Absorbance at 1724 $cm^{-1}$ | 0.003 | 0.005 |

TABLE 2

| INGREDIENTS (wt. %) | EXAMPLE 3 | EXAMPLE 4 | EXAMPLE 5 |
|---|---|---|---|
| SDA 3C ethanol | 74.1 | 74.1 | 74.1 |
| PEG-12 dimethicone | 2.25 | 2.25 | 2.25 |

TABLE 2-continued

| INGREDIENTS (wt. %) | EXAMPLE 3 | EXAMPLE 4 | EXAMPLE 5 |
|---|---|---|---|
| Glycerin | 0.5 | 1.0 | 1.5 |
| Caprylyl glycol | 0.5 | 0.5 | 0.5 |
| Fragrance | 0.075 | 0.075 | 0.075 |
| Water | q.s. | q.s. | q.s. |
| FTIR (2 week contact time) Absorbance at 1724 cm$^{-1}$ | 0.019 | 0.011 | 0.008 |

TABLE 3

| INGREDIENTS (wt. %) | EXAMPLE 6 | EXAMPLE 7 |
|---|---|---|
| SDA 3C ethanol | 74.1 | 74.1 |
| PEG-12 dimethicone | 1.25 | 1.25 |
| Glycerin | 1.5 | 1.0 |
| Caprylyl glycol | 0.5 | 0.5 |
| Fragrance | 0.075 | 0.075 |
| Water | q.s. | q.s. |
| FTIR (1 day contact time) Absorbance at 1724 cm$^{-1}$ | 0.007 | 0.022 |
| FTIR (2 week contact time) Absorbance at 1724 cm$^{-1}$ | 0.007 | 0.024 |

TABLE 4

| INGREDIENTS (wt. %) | EXAMPLE 8 | EXAMPLE 9 | EXAMPLE 10 |
|---|---|---|---|
| SDA 3C ethanol | 74.1 | 74.1 | 74.1 |
| PEG-12 dimethicone | 1.75 | 1.75 | 1.75 |
| Glycerin | 0.25 | 0.5 | 1.0 |
| Caprylyl glycol | 0.5 | 0.5 | 0.5 |
| Fragrance | 0.075 | 0.075 | 0.075 |
| Water | q.s. | q.s. | q.s. |
| TACK (grams) | 153 | 63 | 27 |

Various modifications and alterations that do not depart from the scope and spirit of this invention will become apparent to those skilled in the art. This invention is not to be duly limited to the illustrative embodiments set forth herein.

We claim:

1. A method for measuring the tack of a surface to indicate the interaction of a disinfecting composition with a floor wax, the method comprising the steps of:
    coating a surface with floor wax,
    allowing the coating to dry,
    applying a selected amount of disinfecting composition to the coated surface, and
    measuring, after a pre-determined amount of time, the tack of the coated surface, by using a controlled force measurement inverted probe machine, wherein a detectable amount of tack indicates that the disinfecting composition has interacted with the floor wax.

2. The method of claim 1, further comprising the steps of allowing the disinfecting composition to dry on the coated surface, thereby forming a disinfectant layer on the coated surface,
    sampling the disinfectant layer, by swabbing or blotting the disinfectant layer,
    testing the sample by Fourier Transform Infrared analysis,
    measuring the absorption of the sample at a pre-selected wavelength that correlates to the floor wax control and that does not correlate to the disinfecting composition, wherein measurable absorbance at said wavelength further indicates that interaction has occurred.

3. The method of claim 1, wherein the disinfecting composition is a foamable alcoholic composition.

4. The method of claim 1, wherein the disinfecting composition comprises:
    at least about 40 wt. % of a $C_{1-6}$ alcohol, based upon the total weight of the disinfecting composition;
    a foaming surfactant selected from the group consisting of fluorosurfactants and siloxane-based polymer surfactants; and
    at least about 0.4 wt. % of glycerin, based upon the total weight of the composition.

5. The method of claim 4, wherein the foaming surfactant is selected from the group consisting of siloxane polymer surfactants.

6. The method of claim 5, wherein the composition comprises from about 0.002 to about 4 wt. % of foaming surfactant, based upon the total weight of the disinfecting composition.

7. The method of claim 5, wherein the amount of glycerin relative to the amount of siloxane polymer surfactant, on a weight basis, is from about 1:0.5 to about 1:7.

8. The method of claim 1, wherein the composition comprises from about 0.4 to about 5 wt. % of glycerin.

9. The method of claim 1, wherein the composition does not interact with floor wax to produce a tack of greater than 130 grams, when tested at standard temperature and pressure, using a controlled force measurement inverted probe machine having a stainless steel flat probe having a diameter of about 0.187 inches, and applying about 100 grams of force for about 5 seconds, after a contact time of about 2 weeks.

10. A foamable disinfecting composition comprising:
    at least about 40 wt. % of a $C_{1-6}$ alcohol, based upon the total weight of the disinfecting composition;
    a foaming surfactant selected from the group consisting of fluorosurfactants and siloxane-based polymer surfactants; and
    from about 0.4 to about 5 wt. % of glycerin, based upon the total weight of the composition, wherein the composition exhibits reduced tack, when applied to a surface that has been coated with a floor wax, when compared to the tack that is exhibited by the same composition but containing less than about 0.4 wt. % of glycerin, based upon the total weight of the composition.

11. The composition of claim 10, wherein the foaming surfactant is selected from the group consisting of siloxane-based polymer surfactants.

12. The composition of claim 10, wherein the composition comprises from about 0.002 to about 4 wt. % of foaming surfactant, based upon the total weight of the disinfecting Composition.

13. The composition of claim 11, wherein the amount of glycerin relative to the amount of siloxane polymer surfactant, on a weight basis, is from about 1:0.5 to about 1:7.

14. A method for measuring the tack of a surface to indicate the interaction of an alcoholic disinfecting composition with a floor wax, the method comprising the steps of:
    coating a surface with floor wax,
    allowing the coating to dry,
    applying an amount of the disinfecting composition to the coated surface, sufficient to form a thin layer over the coated surface,
    measuring, after a pre-determined amount of time, the tack of the coated surface, by using a controlled force measurement inverted probe machine, wherein a detectable amount of tack indicates that the disinfecting composition has interacted with the floor wax, allowing the disinfecting composition to dry, thereby forming a disinfectant layer, sampling the disinfectant layer, by swabbing or blotting the disinfectant layer, testing the sample by Fourier Transform Infrared analysis, measuring the absorption of the sample at a pre-selected wavelength that correlates to the floor wax control and that does not correlate to the disinfecting composition, wherein measurable absorbance at said wavelength provides confirmation that interaction has occurred.

* * * * *